Jan. 18, 1966 E. S. BOERNER Plant Pat. 2,590
ROSE PLANT
Filed Oct. 26, 1964
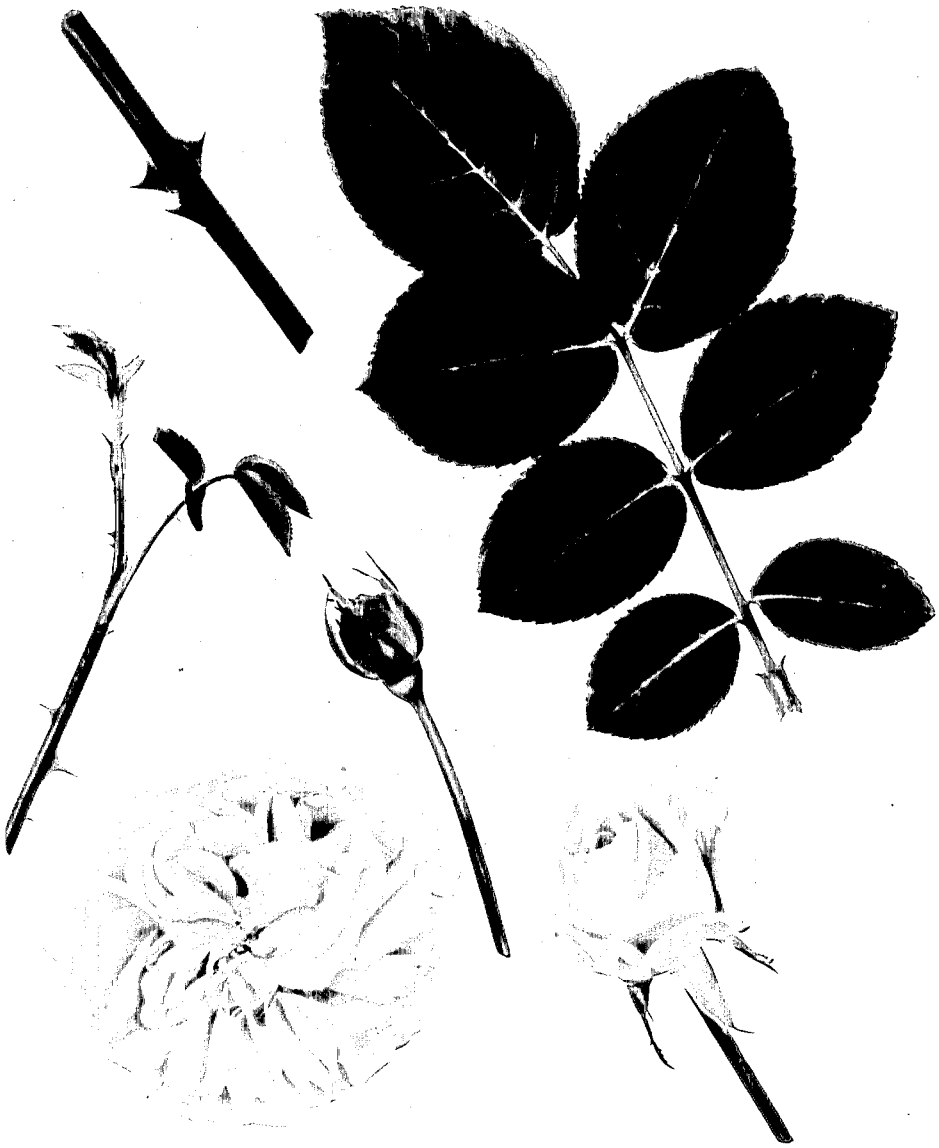
Inventor.
E. S. Boerner
By: Robb & Robb
Attorneys.

United States Patent Office

Plant Pat. 2,590
Patented Jan. 18, 1966

2,590
ROSE PLANT

Eugene S. Boerner, Newark, N.Y., assignor to Jackson & Perkins Company, Newark, N.Y., a corporation of New York Filed Oct. 26, 1964, Ser. No. 406,643
1 Claim. (Cl. Plt.—28)

The present invention relates to a new and distinct variety of rose plant of the floribunda class, which was originated by me by crossing the variety known as "Pink Bountiful" (Plant Patent No. 601) with the variety known as "Spartan" (Plant Patent No. 1,357).

The primary objective of this breeding was to produce a new and improved rose variety comparable to "Spartan," but which bears flowers of larger size, while retaining the floriferousness and the general foliage characteristics of "Spartan." This objective was fully achieved, along with other desirable improvements, as evidenced by the following unique combination of characteristics which are outstanding in the new variety and which distinguish it from its parents, as well as from all other varieties of which I am aware:

(1) General foliage characteristics similar to the parent variety "Spartan";

(2) A floriferous habit;

(3) A habit of bearing the flowers in clusters at the ends of the stems rather than individually;

(4) A flower size greater than that of the variety "Spartan";

(5) A flower petal arrangement which is more full and more symmetrical than that of either of the parent varieties; and (6) A distinctive and attractive general color tonality of the flowers, corresponding to Spectrum Red, very lightly overcast with Scarlet-Red, which is quite different from the flower color of the parent variety "Pink Bountiful" and more nearly like the flower color of "Spartan."

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Pink Bountiful."
*Pollen parent.*—"Spartan."
Classification:
*Botanic.*—Floribunda.
*Commercial.*—Floribunda.

*Flower*

(Observations made from specimens grown outdoors at Newark, New York, in the early morning during the latter part of the month of June.)

Blooming habit: Recurrent—continuous.
Bud:
*Size.*—Medium.
*Form.*—Ovoid pointed; not affected by wet or hot weather.
*Color.*—When sepals first divide—Carmine, Plate 1. When petals begin to unfurl—Carmine, Plate 1, lightly overcast with Spectrum Red, Plate 1. When half-blown: inside of petals—Scarlet-Red, Plate 1; reverse of petals—Spectrum Red, Plate 1, very lightly overcast with Scarlet-Red, Plate 1.
*Sepals.*—Branched; curl back when petals begin to unfurl. Color: inside—Cosse Green, Plate 5; outside—Lettuce Green, Plate 32.
*Calyx.*—Color—Lettuce Green, Plate 32. Shape—funnel. Size—small. Aspect—smooth. Odor when rubbed—none.
*Peduncle.*—Length—medium. Aspect—rough. Strength—erect; slender. Color—Oil Green, Plate 5, very lightly overcast with Buffy Citrine, Plate 16.
*Opening.*—Opens up well; is not affected by adverse weather conditions.
Bloom:
*Size.*—Medium. Average size when fully expanded—from 4 to 4½ inches.
*Borne.*—Several together and in rounded clusters.
*Stems.*—Medium length; strong.
*Form (when first open).*—Full-open. Permanence—retains its form to the end.
*Petalage.*—Double (full but open center). Number of petals under normal conditions—from 30 to 35.
*Color.*—Center of flower—Scarlet-Red, Plate 1. Outer petals—Scarlet-Red, Plate 1, very lightly overcast with Spectrum Red, Plate 1. Base of petals (aiglet)—Light Chalcedony Yellow, Plate 17. Inside of petals—Spectrum Red, Plate 1, very lightly overcast with Scarlet-Red, Plate 1. Reverse of petals—Nopal Red, Plate 1, lightly overcast with Spectrum Red, Plate 1. General tonality from a distance—Scarlet-Red, Plate 1.
*Discoloration.*—General tonality at end of first day—Scarlet-Red, Plate 1. Second day—Spectrum Red, Plate 1, very lightly overcast with Scarlet-Red, Plate 1. Third day—Spectrum Red, Plate 1, very lightly overcast with Scarlet-Red, Plate 1.
Petals:
*Texture.*—Leathery; is not affected by wet or hot weather.
*Appearance.*—Inside—satiny. Outside—shiny.
*Form.*—Oval.
*Arrangement.*—Imbricated (regularly arranged shing-like).
*Petaloids in center.*—Few; small.
*Persistence.*—Drop off cleanly.
*Fragrance.*—Moderate. Nature—tea (average hybrid tea scent).
*Lasting quality.*—On plant—long. As cut flower—long.

*Genital organs*

Stamens, anthers: Medium size; regularly arranged around styles. Color—Vinaceous-Rufous, Plate 14.
Stamens, filaments (threads): Medium length. Color—Chamois, Plate 30.
Pollen: Color—Flesh Color, Plate 14.
Styles: Loosely separated; uneven length; medium length; thin.
Stigmas: Color—Light Ochraceous-Buff, Plate 15.
Ovaries: All enclosed in calyx.
Hips: None.
Seeds: None.

*Plant*

Form: Bush.
Growth: Vigorous; bushy.
Foliage: Compound of 5 to 7 leaflets.
*Size.*—Medium.
*Quantity.*—Abundant.
*Color.*—New foliage: upper side—Lettuce Green, Plate 5, with serrations and center vein Oxblood Red, Plate 1; under side—Carmine, Plate 1, with center of leaf overcast with Cosse Green, Plate 5. Old foliage: upper side—Varley's Green, Plate 18; under side—Chromium Green, Plate 32.

*Shape.*—Oval pointed.

*Texture.*—Upper side—leathery. Under side—smooth.

*Ribs and veins.*—Ordinary.

*Edge.*—Serrated (saw toothed).

*Serration.*—Both double and single; small.

*Leaf stem.*—Color—Absinthe Green, Plate 31. Under side—prickly.

*Stipules.*—Medium length; bearded.

Wood:

*New wood.*—Color—Rainette Green, Plate 31. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of general foliage characteristics similar to the parent variety "Spartan," a floriferous habit, a habit of bearing the flowers in clusters at the ends of the stems, rather than individually, a flower size greater than that of the variety "Spartan," a flower petal arrangement which is more full and more symmetrical than that of either of the parent varieties, and a distinctive and attractive general color tonality of the flowers, corresponding to Spectrum Red, very lightly overcast with Scarlet-Red, which is quite different from the flower color of the parent variety "Pink Bountiful" and more nearly like the flower color of "Spartan."

No references cited.

ABRAHAM G. STONE, *Primary Examiner.*

R. E. BAGWILL, *Assistant Examiner.*